(12) United States Patent
Lippert et al.

(10) Patent No.: US 12,178,975 B2
(45) Date of Patent: Dec. 31, 2024

(54) GUIDEWIRE HAVING ENLARGED, MICRO-FABRICATED DISTAL SECTION

(71) Applicant: SCIENTIA VASCULAR, Inc., West Valley City, UT (US)

(72) Inventors: John A. Lippert, Park City, UT (US); Edward J. Snyder, Park City, UT (US)

(73) Assignee: SCIENTIA VASCULAR, INC., West Valley City, UT (US)

( * ) Notice: Subject to any disclaimer, the term of this patent is extended or adjusted under 35 U.S.C. 154(b) by 750 days.

(21) Appl. No.: 17/154,777

(22) Filed: Jan. 21, 2021

(65) Prior Publication Data

US 2021/0228845 A1 Jul. 29, 2021

Related U.S. Application Data

(60) Provisional application No. 62/965,005, filed on Jan. 23, 2020.

(51) Int. Cl.
*A61M 25/09* (2006.01)
(52) U.S. Cl.
CPC ............ *A61M 25/09041* (2013.01); *A61M 2025/09083* (2013.01); *A61M 2025/09166* (2013.01)
(58) Field of Classification Search
CPC .......... A61M 25/09041; A61M 25/09; A61M 2025/09175; A61M 2025/09083; A61M 2025/09166; A61M 2025/09075; A61M 2025/09108
See application file for complete search history.

(56) References Cited

U.S. PATENT DOCUMENTS

| 2,022,065 | A | 11/1935 | Wappler |
| 2,187,299 | A | 1/1940 | Otto |
| 3,183,702 | A | 5/1965 | Zittell |
| 3,572,334 | A | 3/1971 | Petterson |
| 3,612,058 | A | 10/1971 | Ackerman |
| 3,709,271 | A | 1/1973 | Flory |
| 3,782,233 | A | 1/1974 | Helm |

(Continued)

FOREIGN PATENT DOCUMENTS

| AU | 07230/40 B2 | 8/2000 |
| AU | 733966 B2 | 5/2001 |

(Continued)

OTHER PUBLICATIONS

Final Office Action received for U.S. Appl. No. 16/281,046, mailed on May 11, 2021, 18 pages.

(Continued)

*Primary Examiner* — Nathan R Price
*Assistant Examiner* — Haden Matthew Ritchie
(74) *Attorney, Agent, or Firm* — Workman Nydegger (57) ABSTRACT

Disclosed is a guidewire having a core wire and an outer tube within which the distal section of the core is inserted. The outer diameter of the tube is greater than the outer diameter of the proximal section of the core wire. The guidewire also includes a proximal coil and a distal, radiopaque coil each disposed over the distal section of the core. A bushing coil is disposed over the proximal coil and distal coil. The proximal coil, distal coil, and bushing coil aid in filling the annular space between the core and the tube and thereby centering and aligning the core and tube.

18 Claims, 4 Drawing Sheets

(56) References Cited

U.S. PATENT DOCUMENTS

| | | |
|---|---|---|
| 3,920,058 A | 11/1975 | Walker |
| 4,163,406 A | 8/1979 | Crawford |
| 4,239,069 A | 12/1980 | Zimmerman |
| 4,416,312 A | 11/1983 | Destberg |
| 4,688,540 A | 8/1987 | Ono |
| 4,719,924 A | 1/1988 | Crittenden et al. |
| 4,801,297 A | 1/1989 | Mueller |
| 4,846,186 A | 7/1989 | Box et al. |
| 4,895,168 A | 1/1990 | Machek |
| 4,989,608 A | 2/1991 | Ratner |
| 5,047,045 A | 9/1991 | Arney et al. |
| 5,069,217 A | 12/1991 | Fleischhacker, Jr. |
| 5,084,022 A | 1/1992 | Claude |
| 5,095,915 A | 3/1992 | Engelson |
| 5,102,390 A | 4/1992 | Crittenden et al. |
| 5,144,959 A | 9/1992 | Gambale et al. |
| 5,147,317 A | 9/1992 | Shank et al. |
| 5,154,725 A | 10/1992 | Leopold |
| 5,174,302 A | 12/1992 | Palmer |
| 5,315,996 A | 5/1994 | Lundquist |
| 5,326,374 A | 7/1994 | Ilbawi et al. |
| 5,345,945 A | 9/1994 | Hodgson et al. |
| 5,372,587 A | 12/1994 | Hammerslag et al. |
| 5,381,782 A | 1/1995 | Delarama et al. |
| 5,382,259 A | 1/1995 | Phelps et al. |
| 5,385,152 A | 1/1995 | Abele et al. |
| 5,437,288 A | 8/1995 | Schwartz et al. |
| 5,441,483 A | 8/1995 | Avitall |
| D363,544 S | 10/1995 | Rowland et al. |
| D363,776 S | 10/1995 | Rowland et al. |
| 5,506,682 A | 4/1996 | Pryor |
| 5,507,751 A | 4/1996 | Goode et al. |
| 5,551,444 A | 9/1996 | Finlayson |
| 5,554,114 A | 9/1996 | Wallace et al. |
| 5,569,218 A | 10/1996 | Berg |
| 5,573,520 A | 11/1996 | Schwartz et al. |
| 5,573,867 A | 11/1996 | Zafred et al. |
| 5,606,981 A | 3/1997 | Tartacower et al. |
| 5,659,205 A | 8/1997 | Weisser |
| 5,673,707 A | 10/1997 | Chandrasekaran |
| 5,676,659 A | 10/1997 | McGurk |
| 5,685,568 A | 11/1997 | Pirrello |
| 5,685,868 A | 11/1997 | Lundquist |
| 5,690,120 A | 11/1997 | Jacobsen et al. |
| 5,706,826 A | 1/1998 | Schwager |
| 5,741,429 A | 4/1998 | Donadio et al. |
| 5,746,701 A | 5/1998 | Noone |
| 5,792,154 A | 8/1998 | Doan et al. |
| 5,797,857 A | 8/1998 | Obitsu |
| 5,800,454 A | 9/1998 | Jacobsen et al. |
| 5,833,631 A | 11/1998 | Nguyen |
| 5,833,632 A | 11/1998 | Jacobsen et al. |
| 5,842,461 A | 12/1998 | Azuma |
| 5,860,963 A | 1/1999 | Azam et al. |
| 5,876,356 A | 3/1999 | Viera et al. |
| 5,911,715 A | 6/1999 | Berg et al. |
| 5,911,717 A | 6/1999 | Jacobsen et al. |
| 5,916,194 A | 6/1999 | Jacobsen et al. |
| 5,931,830 A | 8/1999 | Jacobsen et al. |
| 5,954,672 A | 9/1999 | Schwager |
| 6,004,279 A | 12/1999 | Crowley et al. |
| 6,014,919 A | 1/2000 | Jacobsen |
| 6,017,319 A | 1/2000 | Jacobsen et al. |
| 6,022,343 A | 2/2000 | Johnson et al. |
| 6,022,369 A | 2/2000 | Jacobsen et al. |
| 6,027,863 A | 2/2000 | Donadio, III |
| 6,033,288 A | 3/2000 | Weisshaus et al. |
| 6,033,394 A | 3/2000 | Vidlund et al. |
| 6,056,702 A | 5/2000 | Lorenzo |
| 6,063,101 A | 5/2000 | Jacobsen et al. |
| 6,110,164 A | 8/2000 | Vidlund |
| 6,132,389 A | 10/2000 | Cornish et al. |
| 6,139,511 A | 10/2000 | Huter et al. |
| D435,909 S | 1/2001 | Ogino et al. |
| 6,168,570 B1 | 1/2001 | Ferrera |
| 6,179,828 B1 | 1/2001 | Mottola et al. |
| 6,183,410 B1 | 2/2001 | Jacobsen et al. |
| 6,183,420 B1 | 2/2001 | Douk et al. |
| 6,214,042 B1 | 4/2001 | Jacobsen et al. |
| 6,228,073 B1 | 5/2001 | Noone et al. |
| 6,245,030 B1 | 6/2001 | Dubois et al. |
| 6,251,086 B1 | 6/2001 | Cornelius et al. |
| 6,260,458 B1 | 7/2001 | Jacobsen et al. |
| 6,261,246 B1 | 7/2001 | Pantages et al. |
| 6,273,881 B1 | 8/2001 | Kiemeneij |
| 6,302,870 B1 | 10/2001 | Jacobsen et al. |
| 6,306,105 B1 | 10/2001 | Rooney et al. |
| 6,346,091 B1 | 2/2002 | Jacobsen et al. |
| 6,356,791 B1 | 3/2002 | Westlund et al. |
| 6,402,706 B2 | 6/2002 | Richardson et al. |
| 6,428,489 B1 | 8/2002 | Jacobsen et al. |
| 6,431,039 B1 | 8/2002 | Jacobsen et al. |
| 6,436,056 B1 | 8/2002 | Wang et al. |
| 6,440,088 B1 | 8/2002 | Jacobsen et al. |
| 6,458,867 B1 | 10/2002 | Wang et al. |
| 6,464,651 B1 | 10/2002 | Hiejima et al. |
| 6,492,615 B1 | 12/2002 | Flanagan |
| 6,494,894 B2 | 12/2002 | Mirarchi |
| 6,527,732 B1 | 3/2003 | Strauss et al. |
| 6,527,746 B1 | 3/2003 | Oslund et al. |
| 6,553,880 B2 | 4/2003 | Jacobsen et al. |
| 6,554,820 B1 | 4/2003 | Wendlandt et al. |
| 6,558,355 B1 | 5/2003 | Metzger et al. |
| 6,579,246 B2 | 6/2003 | Jacobsen et al. |
| 6,602,207 B1 | 8/2003 | Mam et al. |
| 6,606,985 B2 | 8/2003 | Negishi |
| 6,610,046 B1 | 8/2003 | Usami et al. |
| 6,627,724 B2 | 9/2003 | Meijs et al. |
| 6,652,508 B2 | 11/2003 | Griffin et al. |
| 6,671,560 B2 | 12/2003 | Westlund et al. |
| 6,766,720 B1 | 7/2004 | Jacobsen et al. |
| 6,805,676 B2 | 10/2004 | Klint |
| 6,866,642 B2 | 3/2005 | Kellerman et al. |
| RE39,018 E | 3/2006 | Azuma et al. |
| 7,024,885 B2 | 4/2006 | Villalobos |
| 7,097,624 B2 | 8/2006 | Campion et al. |
| 7,110,910 B1 | 9/2006 | Deffenbaugh et al. |
| 7,128,718 B2 | 10/2006 | Hojeibane et al. |
| 7,172,587 B2 | 2/2007 | Poole et al. |
| 7,182,735 B2 | 2/2007 | Shireman et al. |
| 7,276,062 B2 | 10/2007 | McDaniel et al. |
| 7,338,345 B2 | 3/2008 | Fujinami |
| 7,421,929 B2 | 9/2008 | French |
| 7,494,474 B2 | 2/2009 | Richardson et al. |
| 7,507,246 B2 | 3/2009 | McGuckin et al. |
| D598,094 S | 8/2009 | Alber |
| 7,621,880 B2 | 11/2009 | Ryan et al. |
| 7,637,875 B2 | 12/2009 | Itou |
| 7,641,622 B2 | 1/2010 | Satou et al. |
| D611,596 S | 3/2010 | Kousai et al. |
| 7,670,302 B2 | 3/2010 | Griffin et al. |
| 7,699,792 B2 | 4/2010 | Hofmann et al. |
| 7,722,545 B2 | 5/2010 | Bertsch |
| 7,722,552 B2 | 5/2010 | Aimi et al. |
| 7,744,545 B2 | 6/2010 | Aimi et al. |
| 7,747,314 B2 | 6/2010 | Parins et al. |
| 7,753,859 B2 | 7/2010 | Kinoshita et al. |
| 7,766,896 B2 | 8/2010 | Kornkven et al. |
| 7,769,839 B2 | 8/2010 | Boivie et al. |
| 7,785,273 B2 | 8/2010 | Eskuri |
| 7,789,839 B2 | 9/2010 | Lupton |
| 7,806,837 B2 | 10/2010 | Rasmussen et al. |
| 7,878,984 B2 | 2/2011 | Jacobsen et al. |
| 7,883,474 B1 | 2/2011 | Mirigian et al. |
| 7,914,467 B2 | 3/2011 | Ayman et al. |
| 7,942,832 B2 | 5/2011 | Kanuka et al. |
| 7,989,042 B2 | 8/2011 | Obara et al. |
| 8,007,434 B2 | 8/2011 | Olson |
| 8,043,314 B2 | 10/2011 | Noriega et al. |
| 8,048,004 B2 | 11/2011 | Davis et al. |
| 8,092,444 B2 | 1/2012 | Lentz et al. |
| 8,105,246 B2 | 1/2012 | Voeller et al. |
| 8,128,579 B2 | 3/2012 | Chen et al. |
| 8,128,580 B2 | 3/2012 | Fujimagari et al. |

(56) References Cited

U.S. PATENT DOCUMENTS

| | | |
|---|---|---|
| 8,137,293 B2 | 3/2012 | Zhou et al. |
| 8,167,821 B2 | 5/2012 | Sharrow |
| 8,257,279 B2 | 9/2012 | Jacobsen |
| 8,292,827 B2 | 10/2012 | Musbach et al. |
| 8,292,828 B2 | 10/2012 | Bernhard |
| 8,357,140 B2 | 1/2013 | Majercak et al. |
| 8,376,865 B2 | 2/2013 | Forster et al. |
| 8,376,961 B2 | 2/2013 | Layman et al. |
| 8,377,056 B2 | 2/2013 | Oyola et al. |
| 8,409,114 B2 | 4/2013 | Parins |
| 8,409,169 B1 | 4/2013 | Moss |
| 8,444,577 B2 | 5/2013 | Bunch et al. |
| 8,454,535 B2 | 6/2013 | Majercak et al. |
| 8,460,213 B2 | 6/2013 | Northrop |
| 8,465,469 B2 | 6/2013 | Brightbill |
| 8,468,919 B2 | 6/2013 | Christian et al. |
| 8,500,658 B2 | 8/2013 | Boyle et al. |
| 8,517,959 B2 | 8/2013 | Kurosawa et al. |
| 8,535,243 B2 | 9/2013 | Shireman |
| 8,540,648 B2 | 9/2013 | Bernhard |
| 8,540,668 B2 | 9/2013 | Griffin et al. |
| 8,551,020 B2 | 10/2013 | Chen et al. |
| 8,551,021 B2 | 10/2013 | Voeller et al. |
| 8,556,914 B2 | 10/2013 | Vrba |
| 8,585,643 B2 | 11/2013 | Vo et al. |
| 8,622,931 B2 | 1/2014 | Teague et al. |
| 8,622,933 B2 | 1/2014 | Maki et al. |
| 8,728,075 B2 | 5/2014 | Wu et al. |
| 8,758,269 B2 | 6/2014 | Miyata et al. |
| 8,784,337 B2 | 7/2014 | Voeller et al. |
| 8,795,202 B2 | 8/2014 | Northrop et al. |
| 8,795,254 B2 | 8/2014 | Layman et al. |
| 8,821,477 B2 | 9/2014 | Northrop et al. |
| 8,870,790 B2 | 10/2014 | Davis et al. |
| 8,900,163 B2 | 12/2014 | Jacobsen et al. |
| 8,915,865 B2 | 12/2014 | Jacobsen et al. |
| 8,932,235 B2 | 1/2015 | Jacobsen et al. |
| 8,936,558 B2 | 1/2015 | Jacobsen et al. |
| 8,939,916 B2 | 1/2015 | Jacobsen et al. |
| 8,956,310 B2 | 2/2015 | Miyata et al. |
| 9,011,511 B2 | 4/2015 | Gregorich et al. |
| 9,067,332 B2 | 6/2015 | Lippert et al. |
| 9,067,333 B2 | 6/2015 | Lippert et al. |
| 9,072,873 B2 | 7/2015 | Lippert et al. |
| 9,072,874 B2 | 7/2015 | Northrop et al. |
| D742,000 S | 10/2015 | Kanazawa |
| 9,162,040 B2 | 10/2015 | Vo et al. |
| 9,227,037 B2 | 1/2016 | Northrop |
| 9,364,589 B2 | 6/2016 | Cage et al. |
| 9,375,234 B2 | 6/2016 | Vrba |
| 9,433,762 B2 | 9/2016 | Griffin et al. |
| 9,439,557 B2 | 9/2016 | Boulais |
| 9,550,013 B2 | 1/2017 | Kawasaki |
| 9,616,195 B2 | 4/2017 | Lippert et al. |
| 9,623,212 B2 | 4/2017 | Tano et al. |
| 9,662,798 B2 | 5/2017 | Christian et al. |
| 9,700,702 B2 | 7/2017 | Tano et al. |
| 9,808,595 B2 | 11/2017 | Turnlund et al. |
| 9,839,764 B2 | 12/2017 | Chouinard |
| 9,848,882 B2 | 12/2017 | Lippert |
| D809,138 S | 1/2018 | Khan et al. |
| 9,950,137 B2 | 4/2018 | Lippert et al. |
| 9,999,748 B2 | 6/2018 | Cajamarca et al. |
| 10,028,666 B2 | 7/2018 | Gregorich |
| 10,052,013 B2 | 8/2018 | Boulais |
| 10,149,608 B2 | 12/2018 | Fujitani |
| D839,426 S | 1/2019 | Bajwa |
| D847,335 S | 4/2019 | Kuwada |
| 10,252,024 B2 | 4/2019 | Northrop |
| D855,180 S | 7/2019 | Haefliger |
| 10,350,383 B2 | 7/2019 | Shuman |
| 10,363,389 B2 | 7/2019 | Lippert et al. |
| D855,800 S | 8/2019 | Gabay et al. |
| 10,420,537 B2 | 9/2019 | Salahieh et al. |
| 10,456,556 B2 | 10/2019 | Cabiri |
| 10,639,456 B2 | 5/2020 | Peralta |
| 10,675,444 B2 | 6/2020 | Kauphusman et al. |
| 10,758,710 B2 | 9/2020 | Romano |
| 10,806,893 B2 | 10/2020 | Jaroch |
| 11,007,345 B2 | 5/2021 | Cottone |
| 11,052,226 B2 | 7/2021 | Salahieh et al. |
| 11,052,228 B2 * | 7/2021 | Lippert ............... A61M 25/09 |
| 11,141,566 B2 | 10/2021 | Cabiri |
| D946,148 S | 3/2022 | Takemoto |
| 11,278,704 B2 | 3/2022 | Pleijers |
| 11,471,645 B2 | 10/2022 | McNiven et al. |
| 11,497,512 B2 | 11/2022 | Wallace et al. |
| 11,565,093 B2 | 1/2023 | Kirt et al. |
| D980,427 S | 3/2023 | Method et al. |
| 11,679,236 B2 | 6/2023 | Von et al. |
| 11,724,065 B2 | 8/2023 | Tilson et al. |
| 11,724,068 B2 | 8/2023 | Von et al. |
| 11,759,217 B2 | 9/2023 | Keating et al. |
| 11,766,539 B2 | 9/2023 | Yee et al. |
| D1,014,751 S | 2/2024 | Shih |
| 11,918,753 B2 | 3/2024 | Moquin et al. |
| 11,957,312 B2 | 4/2024 | Boulais |
| 2001/0009980 A1 | 7/2001 | Richardson et al. |
| 2001/0044624 A1 | 11/2001 | Seraj et al. |
| 2002/0013540 A1 | 1/2002 | Jacobsen et al. |
| 2002/0019599 A1 | 2/2002 | Rooney et al. |
| 2002/0049392 A1 | 4/2002 | Demello |
| 2002/0062524 A1 | 5/2002 | Vogland et al. |
| 2002/0068912 A1 | 6/2002 | Merdan |
| 2002/0078808 A1 | 6/2002 | Jacobsen et al. |
| 2002/0082524 A1 | 6/2002 | Anderson et al. |
| 2003/0009208 A1 | 1/2003 | Snyder et al. |
| 2003/0023190 A1 | 1/2003 | Cox |
| 2003/0060732 A1 | 3/2003 | Jacobsen et al. |
| 2003/0069521 A1 | 4/2003 | Reynolds et al. |
| 2003/0069522 A1 | 4/2003 | Jacobsen et al. |
| 2003/0093059 A1 | 5/2003 | Griffin et al. |
| 2003/0125641 A1 | 7/2003 | Jafari et al. |
| 2004/0039371 A1 | 2/2004 | Tockman et al. |
| 2004/0054349 A1 | 3/2004 | Brightbill |
| 2004/0087933 A1 | 5/2004 | Lee et al. |
| 2004/0093060 A1 | 5/2004 | Seguin et al. |
| 2004/0102719 A1 | 5/2004 | Keith et al. |
| 2004/0102720 A1 | 5/2004 | Kellerman et al. |
| 2004/0111044 A1 | 6/2004 | Davis et al. |
| 2004/0122340 A1* | 6/2004 | Vrba ............... A61M 25/09 600/585 |
| 2004/0167437 A1 | 8/2004 | Sharrow et al. |
| 2004/0167440 A1 | 8/2004 | Sharrow |
| 2004/0167443 A1 | 8/2004 | Shireman et al. |
| 2004/0171996 A1 | 9/2004 | Kiemeneij |
| 2004/0181174 A2 | 9/2004 | Davis et al. |
| 2004/0186485 A1 | 9/2004 | Kear |
| 2004/0193140 A1 | 9/2004 | Griffin et al. |
| 2004/0225292 A1 | 11/2004 | Sasso et al. |
| 2004/0254450 A1 | 12/2004 | Griffin et al. |
| 2005/0054953 A1 | 3/2005 | Ryan et al. |
| 2005/0065456 A1 | 3/2005 | Eskuri |
| 2005/0124976 A1 | 6/2005 | Devens et al. |
| 2005/0137501 A1 | 6/2005 | Euteneuer et al. |
| 2005/0216049 A1 | 9/2005 | Jones et al. |
| 2005/0274384 A1 | 12/2005 | Tran et al. |
| 2006/0006649 A1 | 1/2006 | Galdonik et al. |
| 2006/0041186 A1 | 2/2006 | Vancaillie |
| 2006/0074442 A1 | 4/2006 | Noriega et al. |
| 2006/0089618 A1 | 4/2006 | McFerran et al. |
| 2006/0112802 A1 | 6/2006 | Fujinami |
| 2006/0121218 A1 | 6/2006 | Obara et al. |
| 2006/0189896 A1 | 8/2006 | Davis et al. |
| 2006/0241519 A1 | 10/2006 | Hojeibane et al. |
| 2006/0247661 A1 | 11/2006 | Richards et al. |
| 2006/0262474 A1 | 11/2006 | Chen et al. |
| 2007/0010786 A1 | 1/2007 | Casey et al. |
| 2007/0055302 A1 | 3/2007 | Henry et al. |
| 2007/0100285 A1 | 5/2007 | Griffin et al. |
| 2007/0112331 A1 | 5/2007 | Weber et al. |
| 2007/0135763 A1 | 6/2007 | Musbach et al. |
| 2007/0142893 A1 | 6/2007 | Buiser et al. |
| 2007/0167876 A1 | 7/2007 | Euteneuer et al. |

(56) References Cited

U.S. PATENT DOCUMENTS

| | | |
|---|---|---|
| 2007/0185415 A1 | 8/2007 | Ressemann et al. |
| 2007/0221230 A1 | 9/2007 | Thompson et al. |
| 2007/0233039 A1 | 10/2007 | Mitelberg |
| 2007/0250036 A1 | 10/2007 | Volk et al. |
| 2007/0282270 A1 | 12/2007 | Mathews et al. |
| 2007/0287955 A1 | 12/2007 | Layman et al. |
| 2008/0021347 A1 | 1/2008 | Jacobsen et al. |
| 2008/0021401 A1* | 1/2008 | Jacobsen ............ A61M 25/0013 604/164.13 |
| 2008/0021404 A1 | 1/2008 | Jacobsen et al. |
| 2008/0021406 A1 | 1/2008 | Jacobsen et al. |
| 2008/0064989 A1 | 3/2008 | Chen et al. |
| 2008/0077049 A1 | 3/2008 | Hirshman |
| 2008/0086854 A1 | 4/2008 | Boyd et al. |
| 2008/0097246 A1 | 4/2008 | Stafford |
| 2008/0097247 A1 | 4/2008 | Eskuri |
| 2008/0097248 A1 | 4/2008 | Munoz et al. |
| 2008/0114303 A1 | 5/2008 | Tremaglio |
| 2008/0119869 A1 | 5/2008 | Teague et al. |
| 2008/0122226 A1 | 5/2008 | Madison |
| 2008/0125674 A1 | 5/2008 | Bilecen et al. |
| 2008/0147170 A1 | 6/2008 | Vrba |
| 2008/0188298 A1 | 8/2008 | Seelig et al. |
| 2008/0188928 A1 | 8/2008 | Salahieh et al. |
| 2008/0200839 A1 | 8/2008 | Bunch et al. |
| 2008/0262474 A1 | 10/2008 | Northrop |
| 2008/0269641 A1 | 10/2008 | O'Shaughnessy et al. |
| 2008/0319525 A1 | 12/2008 | Tieu et al. |
| 2009/0036832 A1 | 2/2009 | Skujins et al. |
| 2009/0036833 A1 | 2/2009 | Parins |
| 2009/0043283 A1 | 2/2009 | Turnlund et al. |
| 2009/0043372 A1 | 2/2009 | Northrop et al. |
| 2009/0118675 A1 | 5/2009 | Czyscon et al. |
| 2009/0118704 A1 | 5/2009 | Sharrow et al. |
| 2009/0177119 A1 | 7/2009 | Heidner et al. |
| 2009/0177185 A1 | 7/2009 | Northrop |
| 2009/0254000 A1* | 10/2009 | Layman ................ A61M 25/01 600/585 |
| 2009/0292225 A1 | 11/2009 | Chen et al. |
| 2009/0318892 A1 | 12/2009 | Aboytes et al. |
| 2010/0063479 A1 | 3/2010 | Merdan et al. |
| 2010/0069882 A1* | 3/2010 | Jennings ............ A61M 25/0158 604/525 |
| 2010/0114017 A1 | 5/2010 | Lenker et al. |
| 2010/0114302 A1 | 5/2010 | Tzafriri et al. |
| 2010/0139465 A1 | 6/2010 | Christian et al. |
| 2010/0145308 A1 | 6/2010 | Layman et al. |
| 2010/0228150 A1 | 9/2010 | Zimmerman et al. |
| 2010/0256527 A1 | 10/2010 | Lippert et al. |
| 2010/0256528 A1 | 10/2010 | Lippert et al. |
| 2010/0256601 A1 | 10/2010 | Lippert et al. |
| 2010/0256602 A1 | 10/2010 | Lippert et al. |
| 2010/0256603 A1 | 10/2010 | Lippert et al. |
| 2010/0256604 A1 | 10/2010 | Lippert et al. |
| 2010/0256605 A1 | 10/2010 | Lippert et al. |
| 2010/0256606 A1 | 10/2010 | Lippert et al. |
| 2010/0318066 A1 | 12/2010 | Miyata et al. |
| 2011/0011226 A1 | 1/2011 | Tsurusawa et al. |
| 2011/0022003 A1 | 1/2011 | Tekulve |
| 2011/0160680 A1 | 6/2011 | Cage et al. |
| 2011/0245807 A1 | 10/2011 | Sakata et al. |
| 2011/0245808 A1 | 10/2011 | Voeller et al. |
| 2011/0251519 A1 | 10/2011 | Romoscanu |
| 2011/0313417 A1 | 12/2011 | De et al. |
| 2012/0046575 A1 | 2/2012 | Brown |
| 2012/0065623 A1 | 3/2012 | Nelson et al. |
| 2012/0158034 A1 | 6/2012 | Wilson et al. |
| 2012/0209073 A1 | 8/2012 | McWeeney et al. |
| 2012/0239074 A1 | 9/2012 | Aboytes et al. |
| 2012/0271397 A1 | 10/2012 | Muzslay et al. |
| 2012/0289938 A1 | 11/2012 | Northrop et al. |
| 2013/0018280 A1 | 1/2013 | Tano et al. |
| 2013/0018359 A1 | 1/2013 | Coyle |
| 2013/0096553 A1 | 4/2013 | Hill et al. |
| 2013/0110000 A1 | 5/2013 | Tully et al. |
| 2013/0131642 A1 | 5/2013 | Miyata et al. |
| 2013/0144267 A1 | 6/2013 | Chan et al. |
| 2013/0184703 A1 | 7/2013 | Shireman et al. |
| 2013/0226033 A1 | 8/2013 | Eskuri |
| 2013/0255456 A1 | 10/2013 | Christian et al. |
| 2014/0012281 A1 | 1/2014 | Wang et al. |
| 2014/0031719 A1 | 1/2014 | Kanazawa |
| 2014/0058324 A1 | 2/2014 | Salahieh et al. |
| 2014/0094787 A1 | 4/2014 | Reynolds |
| 2014/0187983 A1 | 7/2014 | Anderson |
| 2014/0257363 A1 | 9/2014 | Lippert |
| 2014/0276109 A1 | 9/2014 | Gregorich |
| 2014/0276787 A1 | 9/2014 | Wang et al. |
| 2014/0279109 A1 | 9/2014 | Vasquez et al. |
| 2014/0309657 A1 | 10/2014 | Ben-Ami |
| 2014/0336620 A1 | 11/2014 | Ayman et al. |
| 2015/0011834 A1 | 1/2015 | Ayala et al. |
| 2015/0011964 A1 | 1/2015 | Abner et al. |
| 2015/0057639 A1 | 2/2015 | Storbeck et al. |
| 2015/0190614 A1 | 7/2015 | Bernhard |
| 2015/0190615 A1 | 7/2015 | Shaltis |
| 2015/0216533 A1 | 8/2015 | Gray et al. |
| 2015/0238734 A1 | 8/2015 | Kanazawa |
| 2015/0290432 A1 | 10/2015 | Mathews et al. |
| 2015/0297863 A1 | 10/2015 | Hannon et al. |
| 2015/0305710 A1 | 10/2015 | Stigall et al. |
| 2015/0306355 A1 | 10/2015 | Idstrom |
| 2016/0001048 A1 | 1/2016 | Koike |
| 2016/0008585 A1 | 1/2016 | Tano |
| 2016/0045101 A1 | 2/2016 | Nakatate et al. |
| 2016/0058382 A1 | 3/2016 | Burkett et al. |
| 2016/0089128 A1 | 3/2016 | Weber et al. |
| 2016/0113793 A1 | 4/2016 | Nishigishi |
| 2016/0135827 A1 | 5/2016 | Elsesser et al. |
| 2016/0199620 A1 | 7/2016 | Pokorney et al. |
| 2016/0235337 A1 | 8/2016 | Govari et al. |
| 2016/0287054 A1 | 10/2016 | Fujitani |
| 2016/0310702 A1 | 10/2016 | Cabiri |
| 2016/0361520 A1 | 12/2016 | Braun |
| 2016/0367788 A1 | 12/2016 | Jimenez et al. |
| 2016/0375226 A1 | 12/2016 | Nabeshima et al. |
| 2017/0047740 A1 | 2/2017 | Narla |
| 2017/0049594 A1 | 2/2017 | Banas et al. |
| 2017/0136213 A1 | 5/2017 | Kauphusman et al. |
| 2017/0189643 A1 | 7/2017 | Christian et al. |
| 2017/0203076 A1 | 7/2017 | Groneberg et al. |
| 2017/0215954 A1 | 8/2017 | Datta et al. |
| 2017/0234411 A1 | 8/2017 | Dewaele et al. |
| 2017/0281909 A1 | 10/2017 | Northrop et al. |
| 2018/0015260 A1 | 1/2018 | Sano et al. |
| 2018/0015261 A1* | 1/2018 | Lippert .................. A61L 31/18 |
| 2018/0015262 A1 | 1/2018 | Lippert et al. |
| 2018/0015263 A1 | 1/2018 | Lippert et al. |
| 2018/0028177 A1 | 2/2018 | Van et al. |
| 2018/0071496 A1 | 3/2018 | Snyder et al. |
| 2018/0177517 A1 | 6/2018 | Lippert et al. |
| 2018/0185619 A1 | 7/2018 | Batman et al. |
| 2018/0193603 A1 | 7/2018 | Falb et al. |
| 2018/0193607 A1 | 7/2018 | Lippert et al. |
| 2018/0207407 A1 | 7/2018 | Tanigaki |
| 2019/0008639 A1 | 1/2019 | Landon et al. |
| 2019/0105463 A1 | 4/2019 | Christian et al. |
| 2019/0175869 A1 | 6/2019 | Kirt et al. |
| 2019/0255290 A1 | 8/2019 | Snyder et al. |
| 2019/0290883 A1 | 9/2019 | Lippert et al. |
| 2019/0358434 A1 | 11/2019 | Fuller et al. |
| 2020/0016378 A1 | 1/2020 | Williams et al. |
| 2020/0054860 A1 | 2/2020 | McElhaney et al. |
| 2020/0094027 A1 | 3/2020 | Davis |
| 2020/0121308 A1 | 4/2020 | Davis et al. |
| 2020/0222666 A1 | 7/2020 | Chan et al. |
| 2020/0222672 A1 | 7/2020 | Davis et al. |
| 2020/0330734 A1 | 10/2020 | Sugita et al. |
| 2020/0345975 A1 | 11/2020 | Snyder |
| 2021/0022748 A1 | 1/2021 | Lorenzo |
| 2021/0162184 A1 | 6/2021 | Lippert et al. |
| 2021/0178128 A1 | 6/2021 | Lippert et al. |
| 2021/0213241 A1 | 7/2021 | Christian et al. |
| 2021/0283372 A1 | 9/2021 | Murphy |

(56) References Cited

U.S. PATENT DOCUMENTS

| | | |
|---|---|---|
| 2021/0283380 A1 | 9/2021 | Lippert et al. |
| 2021/0307766 A1 | 10/2021 | Keating et al. |
| 2021/0346656 A1 | 11/2021 | Lippert et al. |
| 2022/0039644 A1 | 2/2022 | Dayton et al. |
| 2022/0047845 A1 | 2/2022 | Niederhauser et al. |
| 2022/0105312 A1 | 4/2022 | Davis |
| 2022/0105318 A1 | 4/2022 | Davis et al. |
| 2022/0118225 A1 | 4/2022 | Snyder et al. |
| 2022/0176075 A1 | 6/2022 | Mcdermott et al. |
| 2022/0218358 A1 | 7/2022 | Dagan et al. |
| 2022/0273474 A1 | 9/2022 | Koop et al. |
| 2022/0280147 A1 | 9/2022 | Davis |
| 2022/0296850 A1 | 9/2022 | Lippert |
| 2022/0323166 A1 | 10/2022 | Tilson et al. |
| 2022/0378459 A1 | 12/2022 | Lippert |
| 2023/0010697 A1 | 1/2023 | Sharma et al. |
| 2023/0069698 A1 | 3/2023 | Hallauer et al. |
| 2023/0071512 A1 | 3/2023 | Maggio et al. |
| 2023/0082226 A1 | 3/2023 | Lippert et al. |
| 2023/0285720 A1 | 9/2023 | Isogai |
| 2023/0405276 A1 | 12/2023 | Cabiri |
| 2024/0123196 A1 | 4/2024 | Lippert et al. |
| 2024/0198059 A1 | 6/2024 | Lippert et al. |
| 2024/0299710 A1 | 9/2024 | Davis et al. |

FOREIGN PATENT DOCUMENTS

| | | |
|---|---|---|
| AU | 07745/59 B2 | 7/2004 |
| AU | 2008229892 A1 | 10/2008 |
| BR | 9709363 A | 1/2000 |
| BR | 9712829 A | 1/2000 |
| CA | 2255781 A1 | 11/1997 |
| CA | 2266685 A1 | 3/1998 |
| CA | 2395149 A1 | 6/2001 |
| CN | 1225282 A | 8/1999 |
| CN | 1230914 A | 10/1999 |
| CN | 1324285 A | 11/2001 |
| CN | 1422673 A | 6/2003 |
| CN | 1518428 A | 8/2004 |
| CN | 1781684 A | 6/2006 |
| CN | 1897892 A | 1/2007 |
| CN | 101001660 A | 7/2007 |
| CN | 101209365 A | 7/2008 |
| CN | 101304778 A | 11/2008 |
| CN | 201239164 Y | 5/2009 |
| CN | 101815553 A | 8/2010 |
| CN | 102049085 A | 5/2011 |
| CN | 102107041 A | 6/2011 |
| CN | 102548603 A | 7/2012 |
| CN | 102639303 A | 8/2012 |
| CN | 102824681 A | 12/2012 |
| CN | 102847225 A | 1/2013 |
| CN | 103301553 A | 9/2013 |
| CN | 103764012 A | 4/2014 |
| CN | 103860265 A | 6/2014 |
| CN | 104271035 A | 1/2015 |
| CN | 104427950 A | 3/2015 |
| CN | 104602616 A | 5/2015 |
| CN | 104602718 A | 5/2015 |
| CN | 104759022 A | 7/2015 |
| CN | 105209102 A | 12/2015 |
| CN | 105361918 A | 3/2016 |
| CN | 105545375 A | 5/2016 |
| CN | 105582611 A | 5/2016 |
| CN | 105682725 A | 6/2016 |
| CN | 105682729 A | 6/2016 |
| CN | 105828690 A | 8/2016 |
| CN | 105979880 A | 9/2016 |
| CN | 107206216 A | 9/2017 |
| CN | 109125889 A | 1/2019 |
| CN | 109715245 A | 5/2019 |
| CN | 109789296 A | 5/2019 |
| DE | 60036882 T2 | 7/2008 |
| DE | 69738235 T2 | 7/2008 |
| EP | 0521595 A2 | 1/1993 |
| EP | 0921754 A1 | 6/1999 |
| EP | 0998323 A1 | 5/2000 |
| EP | 0934141 B1 | 11/2005 |
| EP | 1239901 B1 | 10/2007 |
| EP | 1844911 A1 | 10/2007 |
| EP | 1940498 A1 | 7/2008 |
| EP | 2964305 A2 | 1/2016 |
| EP | 2414022 B1 | 8/2017 |
| ES | 2293660 T3 | 3/2008 |
| GB | 2478988 A | 9/2011 |
| JP | 59-102509 A | 6/1984 |
| JP | 06-154335 A | 6/1994 |
| JP | 07-008560 A | 1/1995 |
| JP | 08-215313 A | 8/1996 |
| JP | 08-243169 A | 9/1996 |
| JP | 08-308934 A | 11/1996 |
| JP | 09-288239 A | 11/1997 |
| JP | 11-294497 A | 10/1999 |
| JP | 2000-116787 A | 4/2000 |
| JP | 2000-126301 A | 5/2000 |
| JP | 2000-511094 A | 8/2000 |
| JP | 2000-343313 A | 12/2000 |
| JP | 2001-500808 A | 1/2001 |
| JP | 2002-543896 A | 12/2002 |
| JP | 2003-011117 A | 1/2003 |
| JP | 2004-025340 A | 1/2004 |
| JP | 2004-136121 A | 5/2004 |
| JP | 2004-329552 A | 11/2004 |
| JP | 2004-535233 A | 11/2004 |
| JP | 2005-514115 A | 5/2005 |
| JP | 2005-533594 A | 11/2005 |
| JP | 2005-534407 A | 11/2005 |
| JP | 2007-514458 A | 6/2007 |
| JP | 2007-313638 A | 12/2007 |
| JP | 2008-178656 A | 8/2008 |
| JP | 2008-536639 A | 9/2008 |
| JP | 2010-029736 A | 2/2010 |
| JP | 2010-503484 A | 2/2010 |
| JP | 2010-535583 A | 11/2010 |
| JP | 2010-535588 A | 11/2010 |
| JP | 2011-206175 A | 10/2011 |
| JP | 4805208 B2 | 11/2011 |
| JP | 4845313 B2 | 12/2011 |
| JP | 2012-502743 A | 2/2012 |
| JP | 2012-522607 A | 9/2012 |
| JP | 2013-106854 A | 6/2013 |
| JP | 2013-523282 A | 6/2013 |
| JP | 2013-176560 A | 9/2013 |
| JP | 2014-023727 A | 2/2014 |
| JP | 2015-073861 A | 4/2015 |
| JP | 2015-181723 A | 10/2015 |
| JP | 2015-186427 A | 10/2015 |
| JP | 2016-013269 A | 1/2016 |
| JP | 2017-169253 A | 9/2017 |
| KR | 2000-0015896 A | 3/2000 |
| KR | 10-2000-0036139 A | 6/2000 |
| NL | 2017570 B1 | 4/2018 |
| RU | 91674 U1 | 2/2010 |
| TW | 412468 B | 11/2000 |
| WO | 94/06503 A1 | 3/1994 |
| WO | 94/19039 A1 | 9/1994 |
| WO | 95/24237 A2 | 9/1995 |
| WO | 97/43949 A1 | 11/1997 |
| WO | 98/55173 A1 | 12/1998 |
| WO | 98/58697 A1 | 12/1998 |
| WO | 99/04847 A1 | 2/1999 |
| WO | 99/53824 A2 | 10/1999 |
| WO | 2004/011076 A2 | 2/2004 |
| WO | 2006/025931 A1 | 3/2006 |
| WO | 2006/058234 A2 | 6/2006 |
| WO | 2006/113863 A2 | 10/2006 |
| WO | 2007/050718 A2 | 5/2007 |
| WO | 2008/034010 A2 | 3/2008 |
| WO | 2009/020691 A2 | 2/2009 |
| WO | 2009/020836 A1 | 2/2009 |
| WO | 2009/020961 A1 | 2/2009 |
| WO | 2009/020962 A1 | 2/2009 |
| WO | 2009/143160 A1 | 11/2009 |
| WO | 2010/077692 A2 | 7/2010 |

(56) References Cited

FOREIGN PATENT DOCUMENTS

| WO | 2010/115163 | A1 | 10/2010 |
|----|-------------|----|---------|
| WO | 2011/123689 | A1 | 10/2011 |
| WO | 2014/005095 | A1 | 1/2014 |
| WO | 2014/066104 | A1 | 5/2014 |
| WO | 2014/138580 | A2 | 9/2014 |
| WO | 2016/047499 | A1 | 3/2016 |
| WO | 2016/117238 | A1 | 7/2016 |
| WO | 2016/136609 | A1 | 9/2016 |
| WO | 2016/152194 | A1 | 9/2016 |
| WO | 2016/158671 | A1 | 10/2016 |
| WO | 2017/151292 | A1 | 9/2017 |
| WO | 2018/017349 | A1 | 1/2018 |
| WO | 2018/017351 | A1 | 1/2018 |
| WO | 2018/218216 |    | 11/2018 |
| WO | 2020/217171 | A1 | 10/2020 |
| WO | 2022/159139 | A1 | 7/2022 |

OTHER PUBLICATIONS

International Search Report and Written Opinion for PCT/US2019/021031 mailed on Jun. 18, 2019.
International Search Report and Written Opinion received for PCT Patent Application No. PCT/US21/14656, mailed on Apr. 28, 2021, 8 pages.
Final Office Action received for U.S. Appl. No. 16/742,211, mailed on Mar. 14, 2023, 22 pages.
Final Office Action received for U.S. Appl. No. 16/855,366, mailed on Dec. 8, 2022, 18 pages.
International Search Report and Written Opinion received for PCT Patent Application No. PCT/US2021/053647, mailed on Dec. 28, 2021, 9 pages.
International Search Report and Written Opinion received for PCT Patent Application No. PCT/US2021/053652, mailed on Dec. 28, 2021, 9 pages.
Non-Final Office Action received for U.S. Appl. No. 17/177,782, mailed on Jan. 23, 2023, 14 pages.
Final Office Action received for U.S. Appl. No. 15/848,878, mailed on Sep. 22, 2021, 12 pages.
Final Office Action received for U.S. Appl. No. 16/616,220, mailed on Oct. 12, 2022, 17 pages.
Final Office Action received for U.S. Appl. No. 17/216,127, mailed on Jun. 13, 2022, 8 pages.
International Search Report and Written Opinion received for PCT Patent Application No. PCT/US21/042753, mailed on Nov. 5, 2021, 14 pages.
Non-Final Office Action received for U.S. Appl. No. 16/616,139, mailed on Oct. 26, 2021, 11 pages.
Non-Final Office Action received for U.S. Appl. No. 16/616,220, mailed on Jun. 3, 2022, 20 pages.
Non-Final Office Action received for U.S. Appl. No. 16/742,211, mailed on Aug. 15, 2022, 20 pages.
Non-Final Office Action received for U.S. Appl. No. 16/855,366, mailed on Jul. 11, 2022, 13 pages.
Non-Final Office Action received for U.S. Appl. No. 16/855,366, mailed on Jun. 23, 2021, 15 pages.
Non-Final Office Action received for U.S. Appl. No. 17/177,782, mailed on Nov. 4, 2022, 7 pages.
Final Office Action received for U.S. Appl. No. 12/753,831, mailed on May 31, 2012.
Final Office Action received for U.S. Appl. No. 12/753,836 mailed on Feb. 17, 2016.
Final Office Action received for U.S. Appl. No. 16/212,425, mailed on Aug. 3, 2020, 14 pages.
Final Office Action received for U.S. Appl. No. 12/753,831, mailed on Aug. 29, 2014.
Final Office Action received for U.S. Appl. No. 12/753,836, mailed on Jan. 9, 2015.
Final Office Action received for U.S. Appl. No. 12/753,836, mailed on May 1, 2012.
Final Office Action received for U.S. Appl. No. 12/753,849, mailed on Jun. 6, 2012.
Final Office Action received for U.S. Appl. No. 12/753,849, mailed on Oct. 9, 2013.
Final Office Action received for U.S. Appl. No. 12/753,855, mailed on Apr. 18, 2012.
Final Office Action received for U.S. Appl. No. 12/753,855, mailed on Jan. 13, 2015.
Final Office Action received for U.S. Appl. No. 12/753,858, mailed on Jan. 17, 2014.
Final Office Action received for U.S. Appl. No. 12/753,858, mailed on Jul. 18, 2012.
Final Office Action received for U.S. Appl. No. 12/753,858, mailed on May 28, 2015.
Final Office Action received for U.S. Appl. No. 12/753,858, mailed on Oct. 19, 2011.
Final Office Action received for U.S. Appl. No. 12/753,858, mailed on Oct. 20, 2017.
Final Office Action received for U.S. Appl. No. 12/753,836, mailed on Jul. 14, 2017.
Final Office Action received for U.S. Appl. No. 15/606,607 mailed on Nov. 19, 2019.
Final Office Action received for U.S. Appl. No. 15/848,878, mailed on Aug. 27, 2020, 13 pages.
Final Office Action received for U.S. Appl. No. 12/753,858, mailed on Nov. 14, 2018.
Final Office Action received for U.S. Appl. No. 12/753,839 mailed on May 31, 2012.
Final Office Action received for U.S. Appl. No. 14/199,675, mailed on May 18, 2017.
Final Office Action received for U.S. Appl. No. 15/611,328, mailed on Sep. 24, 2019.
Final Office Action received for U.S. Appl. No. 15/611,344, mailed on Nov. 12, 2019.
Final Office Action received for U.S. Appl. No. 15/698,553, mailed on Nov. 27, 2019.
Final Rejection received for U.S. Appl. No. 15/606,607, mailed on Dec. 15, 2020, 24 pages.
International Search Report and Written Opinion for application No. PCT/US17/41299 dated Oct. 2, 2017.
International Search Report and Written Opinion for application No. PCT/US17/41301 dated Oct. 2, 2017.
International Search Report and Written Opinion for application No. PCT/US17/41305 dated Oct. 2, 2017.
International Search Report and Written Opinion for Application PCT/US2017/050602 mailed on Nov. 7, 2017.
International Search Report and Written Opinion for application PCT/US2017/050802 dated Nov. 7, 2017.
International Search Report and Written Opinion for application PCT/US2017/050802 mailed on Nov. 7, 2017.
International Search Report and Written Opinion for PCT/US2009/067217 dated Dec. 16, 2010.
International Search Report and Written Opinion for PCT/US2010/029867 dated Jun. 1, 2010.
International Search Report and Written Opinion for PCT/US2014/021742 dated Aug. 27, 2014.
International Search Report and Written Opinion for PCT/US2017/041299 mailed on Oct. 2, 2017.
International Search Report and Written Opinion for PCT/US2017/041301 mailed on Oct. 2, 2017.
International Search Report and Written Opinion for PCT/US2017/068056 mailed on Feb. 26, 2018.
International Search Report and Written Opinion for PCT/US2018/034723 dated Sep. 5, 2018.
International Search Report and Written Opinion for PCT/US2018/034756 mailed on Aug. 14, 2018.
International Search Report and Written Opinion for PCT/US2019/019046, mailed on May 17, 2019.
International Search Report and Written Opinion issued in PCT/US2018/034723 mailed Sep. 5, 2018.
International Search Report and Written Opinion received for PCT Patent Application No. PCT/US2020/030589, mailed on Jul. 17, 2020, 7 pages.

(56) References Cited

OTHER PUBLICATIONS

International Search Report and Written Opinion, PCT App. No. PCT/US2020/013754, mailed on Jun. 9, 2020, 11 pages.
Non-Final Office Action received for U.S. Appl. No. 15/606,607, mailed on Jun. 10, 2020, 26 pages.
Non-Final Office Action received for U.S. Appl. No. 15/611,328, mailed on Jun. 29, 2020, 13 pages.
Non-Final Office Action received for U.S. Appl. No. 15/917,255, mailed on Aug. 17, 2020, 12 pages.
Non-Final Office Action received for U.S. Appl. No. 16/281,046, mailed on Oct. 29, 2020, 18 pages.
Office Action received for U.S. Appl. No. 12/633,727, mailed on Oct. 16, 2012.
Non-Final Office Action received for U.S. Appl. No. 15/848,878, mailed on Jun. 3, 2021, 13 pages.
Office Action received for European Patent Application No. 19710207.2, mailed on Dec. 4, 2023, 4 pages.
International Search Report and Written Opinion received for PCT Patent Application No. PCT/US22/42514, mailed on Dec. 28, 2022, 11 pages.
International Search Report and Written Opinion received for PCT Patent Application No. PCT/US22/42517, mailed on Feb. 7, 2023, 11 pages.
Supplementary European Search Report received for EP Patent Application No. 21744674.9, mailed on Feb. 7, 2024, 9 pages.
Office Action received for U.S. Appl. No. 12/753,831, mailed on Feb. 1, 2012.
Office Action received for U.S. Appl. No. 12/753,831, mailed on Mar. 21, 2014.
Office Action received for U.S. Appl. No. 12/753,836, mailed on Dec. 9, 2011.
Office Action received for U.S. Appl. No. 12/753,836, mailed on Dec. 23, 2016.
Office Action received for U.S. Appl. No. 12/753,836, mailed on Jul. 31, 2014.
Office Action received for U.S. Appl. No. 12/753,836, mailed on Jun. 26, 2015.
Office Action received for U.S. Appl. No. 12/753,839, mailed on May 5, 2014.
Office Action received for U.S. Appl. No. 12/753,842, mailed on Jan. 29, 2014.
Office Action received for U.S. Appl. No. 12/753,849, mailed on Jan. 3, 2013.
Office Action received for U.S. Appl. No. 12/753,849, mailed on May 10, 2011.
Office Action received for U.S. Appl. No. 12/753,849, mailed on May 27, 2014.
Office Action received for U.S. Appl. No. 12/753,849, mailed on Oct. 18, 2011.
Office Action received for U.S. Appl. No. 12/753,855, mailed on Feb. 28, 2014.
Office Action received for U.S. Appl. No. 12/753,855, mailed on May 21, 2015.
Office Action received for U.S. Appl. No. 12/753,855, mailed on Sep. 15, 2011.
Office Action received for U.S. Appl. No. 12/753,858, mailed on Dec. 30, 2015.
Office Action received for U.S. Appl. No. 12/753,858, mailed on Feb. 3, 2012.
Office Action received for U.S. Appl. No. 12/753,858, mailed on Mar. 13, 2018.
Office Action received for U.S. Appl. No. 12/753,858, mailed on Mar. 27, 2017.
Office Action received for U.S. Appl. No. 12/753,858, mailed on Mar. 29, 2013.
Office Action received for U.S. Appl. No. 12/753,858, mailed on May 10, 2011.
Office Action received for U.S. Appl. No. 12/753,858, mailed on Oct. 24, 2016.
Office Action received for U.S. Appl. No. 12/753,858, mailed on Sep. 4, 2014.
Office Action received for U.S. Appl. No. 13/901,375, mailed on Aug. 1, 2016.
Office Action received for U.S. Appl. No. 13/901,375, mailed on Dec. 10, 2015.
Office Action received for U.S. Appl. No. 15/606,607 mailed on May 14, 2019.
Office Action received for U.S. Appl. No. 15/611,344, mailed on May 21, 2020.
Office Action received for U.S. Appl. No. 15/698,553, mailed on Nov. 27, 2019.
Office Action received for U.S. Appl. No. 15/848,878, mailed on Feb. 5, 2020.
Office Action received for U.S. Appl. No. 16/212,425, mailed on Mar. 16, 2020.
Office Action received for U.S. Appl. No. 12/753,855 mailed on May 5, 2016.
Office Action received for U.S. Appl. No. 14/199,675, mailed on Nov. 3, 2016.
Office Action received for U.S. Appl. No. 15/465,399, mailed on Apr. 23, 2018.
Office Action received for U.S. Appl. No. 15/611,328, mailed on Mar. 27, 2019.
Office Action received for U.S. Appl. No. 15/611,344, mailed on Mar. 26, 2019.
Penumbra Augments Vascular Franchise with Latest Indigo System Launch and Expands Medical/Scientific Leadership, Jul. 14, 2020, https://investors.penumbrainc.com/investors-relations/press-releases/press-release-details/2020/Penumbra-Augments-Vascular-Franchise-with-Latest-Indigo-System-Launch-and-Expands-MedicalScientific-Leadership/default.aspx.
U.S. Appl. No. 12/753,839, filed Feb. 7, 2012, Office Action.
U.S. Appl. No. 12/753,839, filed May 31, 2012, Final Office Action.
U.S. Appl. No. 12/753,842, filed Aug. 1, 2012, Office Action.
U.S. Appl. No. 12/753,842, filed Jan. 9, 2013, Final Office Action.
U.S. Appl. No. 12/753,842, filed Sep. 4, 2014, Final Office Action.
U.S. Appl. No. 12/753,858, filed May 28, 2015, Final Office Action.
Final Office Action received for U.S. Appl. No. 16/855,366, mailed on Jun. 20, 2024, 17 pages.
Final Office Action received for U.S. Appl. No. 17/836,863, mailed on Jun. 25, 2024, 6 pages.
Non-Final Office Action received for U.S. Appl. No. 17/382,271, mailed on May 14, 2024, 22 pages.
Non-Final Office Action received for U.S. Appl. No. 17/493,265, mailed on Jun. 11, 2024, 19 pages.
European Search Report received for EP Patent Application No. 21878402, mailed on Aug. 14, 2024, 13 pages.
Final Office Action received for U.S. Appl. No. 17/382,271, mailed on Sep. 16, 2024, 9 pages.
Non-Final Office Action received for U.S. Appl. No. 17/752,600, mailed on Sep. 10, 2024, 11 pages.
Requirement for Restriction/Election received for U.S. Appl. No. 17/493,281, mailed on Oct. 9, 2024, 13 pages.

* cited by examiner

FIG. 6  FIG. 7

GUIDEWIRE HAVING ENLARGED, MICRO-FABRICATED DISTAL SECTION

CROSS-REFERENCE TO RELATED APPLICATIONS

This application claims priority to and the benefit of U.S. Provisional Patent Application Ser. No. 62/965,005, filed Jan. 23, 2020 and titled "Guidewire Having Enlarged, Micro-Fabricated Distal Section", the entirety of which is incorporated herein by reference.

BACKGROUND

Guidewire devices are often used to lead or guide catheters or other interventional devices to a targeted anatomical location within a patient's body. Typically, guidewires are passed into and through a patient's vasculature in order to reach the target location, which may be at or near the patient's heart or brain, for example. Radiographic imaging is typically utilized to assist in navigating a guidewire to the targeted location. In many instances, a guidewire is placed within the body during the interventional procedure where it can be used to guide multiple catheters or other interventional devices to the targeted anatomical location.

Guidewires are available with various outer diameter sizes. Widely utilized sizes include 0.010, 0.014, 0.016, 0.018, 0.024, 0.035, and 0.038 inches, for example, though they may also be smaller or larger in diameter. Because torque transmission is a function of diameter, larger diameter guidewires typically have greater torque transmission (the ability to effectively transfer torque from proximal portions of the wire to more distal portions of the wire). On the other hand, smaller diameter guidewires typically have greater flexibility.

A catheter used in conjunction with a guidewire will be sized with an inner diameter somewhat larger than the outer diameter of the guidewire to enable the catheter to be positioned over and translated upon the guidewire. The difference in size between the guidewire and catheter can affect the ability of the catheter to travel along the guidewire. For example, the larger the annular space between the outer diameter of the guidewire and the inner diameter of the catheter, the greater the amount of potential radial offset the catheter may experience and the more difficult it may be to navigate the catheter over the guidewire. With excessive radial offset, the distal end of the catheter may have a higher risk of catching against vasculature or other anatomy of the patient rather than smoothly following along the guidewire path.

Often, a guidewire size is selected to minimize the amount of annular space between the guidewire and a given catheter size required or desired for a particular procedure, and to thereby limit the types of issues described above. However, several challenges exist to this approach. For example, increasing the size of the guidewire may overly increase the stiffness of the guidewire as well, potentially to levels that are undesirable for the initial placement of the guidewire at the targeted treatment site. Moreover, while there are known methods for increasing guidewire flexibility, such as reducing the core wire diameter, but these often come at the expense of torquability of the device.

What is needed, therefore, is a guidewire device capable of being manufactured with a relatively large outer diameter, at least at the distal section, that minimizes the annular space between the guidewire and certain sizes of compatible catheters, and that is also capable of providing sufficient flexibility and torquability along its length.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

DETAILED DESCRIPTION

Introduction

Figure 1:
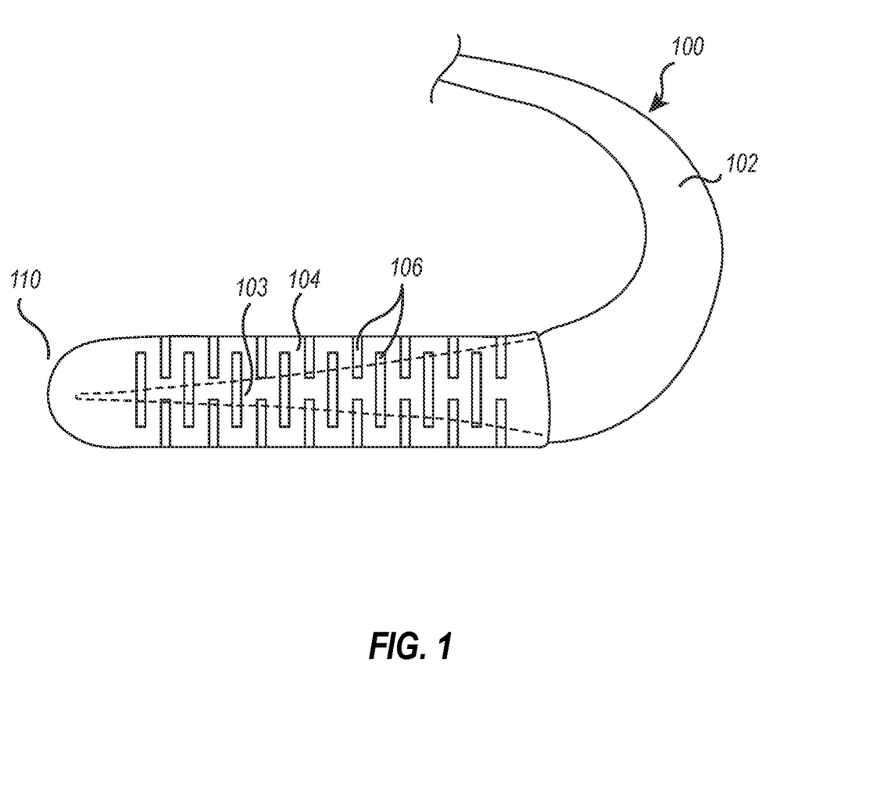
FIG. 1 illustrates an embodiment of a guidewire device having a core and an outer tube and which may utilize one or more of the components described herein.

FIG. 1 schematically illustrates the general components of a guidewire 100 that may utilize one or more features described in greater detail below. The illustrated guidewire 100 includes a core 102 and an outer tube 104. The core 102 includes a distal section 103 (also referred to herein as the distal core 103) that extends into the outer tube 104 as shown. The distal core 103 may be tapered, either continuously or in one or more discrete sections, so that more distal sections have a smaller diameter and greater flexibility than more proximal sections. In some embodiments, the most distal section of the core 102 may be flattened into a ribbon-like shape with a flat, rectangular, or oblong cross section. For example, the distal core 103 may be ground so as to progressively taper to a smaller diameter at the distal end.

The core 102 and the tube 104 are typically formed from different materials. For example, the tube 104 is preferably formed from a relatively flexible and elastic material such as nitinol, whereas the core 102 may be formed from a relatively less flexible and elastic material such as stainless steel. Forming the core 102 from stainless steel (or other materials with similar modulus of elasticity) may be advantageous because it allows the distal tip to hold a shape when selectively bent/shaped by an operator and because stainless steel provides sufficient modulus of elasticity to provide more responsive translational movement. While these materials are presently preferred, other suitable materials such as polymers or other metals/alloys may additionally or alternatively be utilized.

The tube 104 is coupled to the core 102 (e.g., using adhesive, soldering, and/or welding) in a manner that beneficially allows torsional forces to be transmitted from the core 102 to the tube 104 and thereby to be further transmitted distally by the tube 104. A medical grade adhesive or other suitable material may be used to couple the tube 104 to the core wire 102 at the distal end 110 of the device to form an atraumatic covering.

The outer tube 104 may include a cut pattern that forms fenestrations 106 in the tube. The pattern of fenestrations 106 may be arranged to provide desired flexibility characteristics to the tube 104, including the promotion of preferred bending directions, the reduction or elimination of preferred bending directions, or gradient increases in flexibility along the longitudinal axis, for example. Examples of cut patterns and other guidewire device features that may be utilized in the guidewire devices described herein are provided in detail in United States Patent Application Publication Nos. 2018/0193607, 2018/0071496, and 2020/0121308, the entireties of each of which are incorporated herein by this reference.

The proximal section of the guidewire device 100 (the portion extending proximally from the tube 104) extends proximally to a length necessary to provide sufficient guidewire length for delivery to a targeted anatomical area. The guidewire device 100 typically has a length ranging from about 50 cm to about 350 cm, more commonly about 200 cm, depending on particular application needs. The tube 104 may have a length ranging from about 5 cm to about 350 cm, more typically about 15 cm to about 50 cm, such as about 25 cm to about 40 cm.

The guidewire device 100 may have a diameter of about 0.010 inches to about 0.038 inches, though larger or smaller sizes may also be utilized depending on particular application needs. For example, particular embodiments may have outer diameter sizes corresponding to standard guidewire sizes such as 0.014 inches, 0.016 inches, 0.018 inches, 0.024 inches, or other such sizes common to guidewire devices. The distal section 103 of the core 102 may taper to a diameter of about 0.002 inches, or a diameter within a range of about 0.001 to 0.005 inches. In some embodiments, the distal tip may be flattened (e.g., to a rectangular cross section) to further enhance bending flexibility while minimizing reductions in cross-sectional area needed for tensile strength. In such embodiments, the cross section may have dimensions of about 0.001 inches by 0.003 inches, for example. In some embodiments, the tube 104 has a length within a range of about 3 to 350 cm.

Additional features and details regarding the foregoing components are described in further detail below. The following examples may be particularly beneficial in applications where the corresponding catheter is about sized at 0.027 inches or greater, and the guidewire is thus beneficially sized at about 0.024 inches or greater in order to limit the amount of annular space between the inner surface of the catheter and the outer surface of the guidewire, but still allow for relative movement between them. In such implementations, the guidewires described herein are able to provide sufficient diameter in the distal sections of the device to limit the annular space, while still maintaining effective torqueability and lateral flexibility. These sizes are not limiting, however, and the same features and details described below may also be utilized in guidewires that are smaller or larger than 0.024 inches.

Improved Guidewire Device with Enlarged Distal Section

Figure 2:
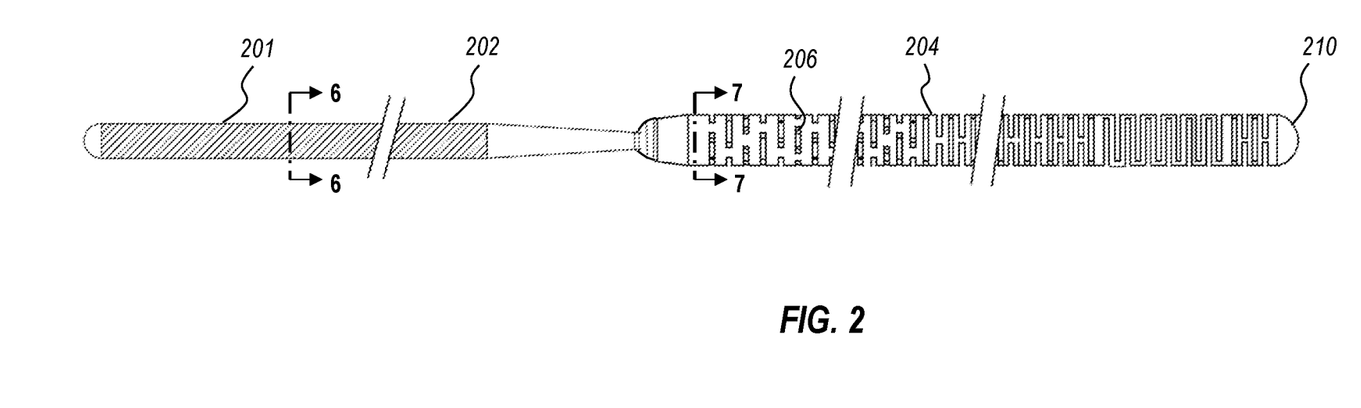
FIG. 2 illustrates an exemplary embodiment of a guidewire device with a tube that has an outer diameter that is larger than an outer diameter of a proximal section of the core.

FIG. 2 illustrates an example of a guidewire 200. Except where noted herein, the guidewire 200 may include any of the general features described above in relation to guidewire 100, with like reference numbers indicating like parts. As shown, the guidewire 200 includes a core 202 and an outer tube 204, with a distal section 203 of the core 202 inserted into the tube 204. The outer tube 204 includes a plurality of fenestrations 206. A polymer-based adhesive may form an atraumatic distal tip 210.

The core 202 also includes a proximal section 201 (also referred to herein as the proximal core 201) that is disposed proximal of the outer tube 204 and is not inserted into the outer tube 204. The proximal core 201 may comprise a friction-lowering coating, such as polytetrafluoroethylene (PTFE) and/or other suitable coating materials. The tube 204 may also include a coating, preferably a suitable hydrophilic coating and/or other suitable coating materials.

Preferably, the outer diameter of the tube 204 is slightly larger than the outer diameter of the proximal core 201. In one exemplary embodiment, the proximal core 201 has an outer diameter of about 0.018 inches, while the tube 204 has an outer diameter of about 0.024 inches. Other core and/or tube sizes may also be utilized, however. Preferably, the tube 204 has an outer diameter that is about 10% or more larger than the outer diameter of the proximal core 201, more preferably about 15% to about 80% larger, or more preferably about 20% to about 70% larger, such as about 25% to about 35% larger.

Figure 6:
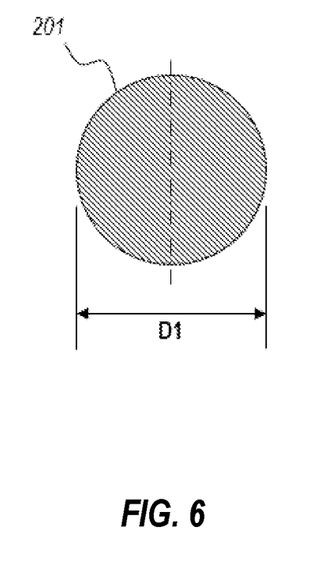
FIGS. 6 and 7 are cross-sectional views of the guidewire of FIG. 2 showing that the outer diameter of the tube is greater than the outer diameter of the proximal section of the core.
Figure 7:
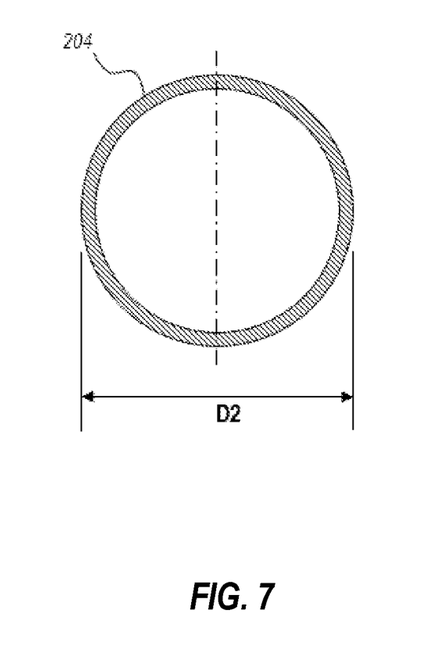

This is further illustrated by the cross-sectional views of FIGS. 6 and 7. As shown, the outer diameter (D1) of the proximal core 201 is less than the outer diameter (D2) of the tube 204. The ratio of D2 to D1 may be, for example, about 1.1 to about 3, more preferably about 1.15 to about 2, or about 1.2 to about 1.75.

As mentioned above, a larger outer diameter in the tube 204 can better match certain desired catheter sizes at the catheter distal tip portion and thereby reduce the amount of annular space between the guidewire and catheter during placement of the catheter over the guidewire. This is particularly beneficial at the more distal sections of the guidewire, which are more likely to be navigated through deeper, more tortuous portions of the patient's vasculature.

However, increasing the diameter of the core 202 to match the larger diameter of the tube 204 may make the core 202 too stiff for use in certain desired applications. Thus, maintaining a smaller core 202, while increasing the size of the tube 204 relative to the core 202, allows use of the more flexible core 202 while still enabling the benefits of a larger tube 204 at the distal sections of the guidewire 200.

As explained in more detail below, however, providing a tube 204 that has a larger outer diameter than the core 202 can introduce other challenges. In particular, the difference in diameter between the outer tube 204 and the distal core 203 enlarges the annular space between the outer surface of the distal core 203 and the inner surface of the tube 204. Because the tube 204 can be more flexible than the distal core 203, as the wire navigates a bend, the distal core 203 may be positioned off-center from the center line of the tube 204. As the guidewire is moved through the vasculature, this off-centering can disrupt the smooth distal transmission of rotational movement, causing a buildup and sudden release of forces which lead the guidewire to move with a "snap" and/or "whip" to a non-desired preferential rotational location. This disruption to the tactile feel and rotational control of the guidewire can make it more difficult for the operator to rotationally position the guidewire as intended, raising the risk of interventional procedure delays, suboptimal outcomes, inability to access the target location, or even tissue injury.

The embodiments described herein beneficially provide additional features that assist in radially centering the distal core 203 within the tube 204 even though the tube 204 has a larger outer diameter than the proximal core 201. One or more centering mechanisms may be included to beneficially reduce undesirable whip and/or snap movements of the guidewire (i.e., the centering mechanisms may improve rotational control), thereby enabling a user to have greater rotational control and improved tactile handling of the guidewire.

Figure 3:
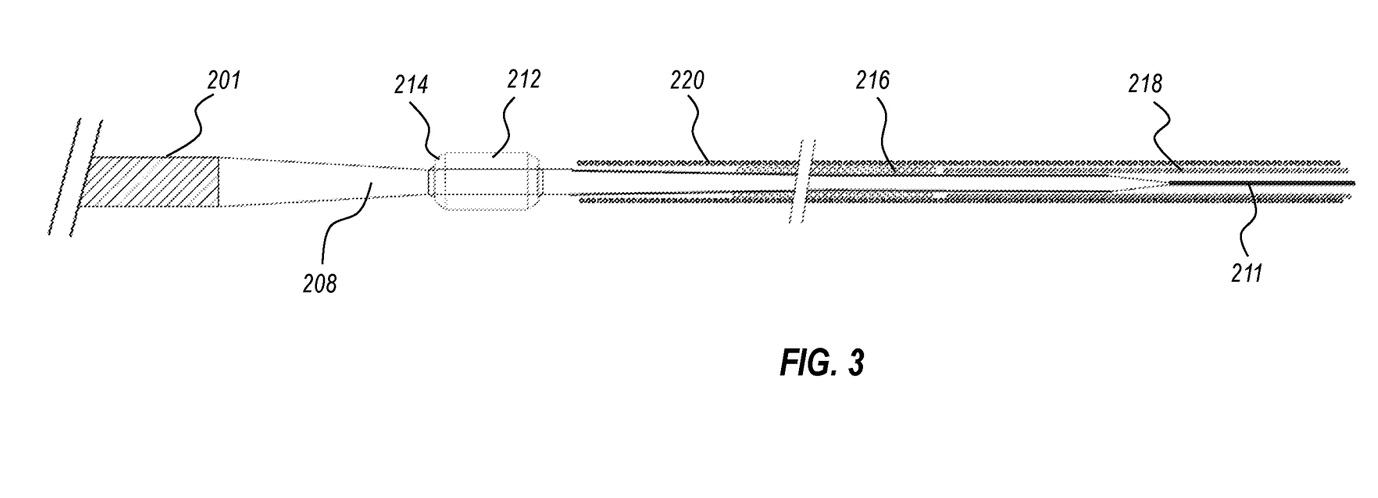
FIG. 3 is a detailed view of the distal section of the guidewire of FIG. 2, with the tube structure removed to better illustrate underlying features of the device.

FIG. 3 illustrates an expanded view of the distal section of the guidewire 200 with the tube 204 removed in order to better visualize the distal core 203 and some of the other underlying components. As shown, the core 202 includes one or more transition zones 208 where the core 202 tapers to a smaller diameter. A distal end section 211 of the core 202 may be flattened. The one or more transition zones 208 may be discrete, with one or more sections of the core of substantially continuous outer diameter disposed between, or the distal core 203 may have a substantially continuous taper along all or most of its length.

A bushing 212 may be included at the point forming the joint to which the proximal end of the tube 204 is attached. The bushing 212 may have an outer diameter that substantially matches the outer diameter of the proximal core 201. The bushing 212 may be formed from the same material as the tube 204 (e.g., nitinol). The bushing 212 provides for better centering between the core 202 and the tube 204 and/or reduces the amount of adhesive needed to bond the separate components. Although shown here as a tube, the bushing 212 may have alternative geometries such as a coil, braid, slotted/cut tube, etcetera.

As shown, the bushing 212 may also include a chamfered or beveled surface 214 on its proximal end to provide a smooth transition between different diameters. The distal end of the bushing 212 may also be chamfered or beveled. Even though the distal end of the bushing 212 will be covered by the tube 204, providing a bushing 212 with a chamfer/bevel on both ends can aid in manufacturing, eliminating the need to ensure proper orientation of the bushing and eliminating the potential for erroneous orientation.

The illustrated guidewire 200 includes a proximal coil 216, a distal coil 218, and a bushing coil 220 positioned over the proximal coil 216 and the distal coil 218. The distal coil 218 is preferably formed of a radiopaque material, such as platinum group, gold, silver, palladium, iridium, osmium, tantalum, tungsten, bismuth, dysprosium, gadolinium, and the like. The distal coil 218 thus preferably allows radiographic visualization of the distal end of the guidewire 200 during a procedure. The distal coil 218 may have a length of about 0.5 cm to about 20 cm, or more typically about 3 cm to about 15 cm, such as about 10 cm.

The proximal coil 216 may be formed from a non-radiopaque material such as stainless steel, other suitable metal, a suitable polymer, or other suitable material. The proximal coil 216 may be attached to the distal core 203 at a point adjacent to or near to the proximal end of the distal coil 218 and/or at any point along the coincident length of the distal core 203, most commonly at or near each end of the proximal coil 216. The proximal coil 216 may have a length of about 1 to 25 cm, or more typically about 3 to 20 cm, such as about 5 to 15 cm. Technically, the distal coil 218 could be extended further proximally to take the place of the proximal coil 216. However, materials that function well as radiopaque markers (e.g., platinum) are relatively expensive. Also, their use as a packing material to fill large portions of the annular space could cause the distal section of the guidewire 200 to be overly bright when imaged under x-ray fluoroscopy and thus not allow the operator to visualize other areas of interest. Thus, the proximal coil 216 is preferably separate from, and formed from a different material than, the distal coil 218.

The proximal coil 216 and the distal coil 218 aid in filling some of the annular space between the distal core 203 and the tube 204. Although the coil examples illustrated herein are shown having wires with a circular cross section, it will be understood that other coil types may also be utilized. For example, centering coil(s) may be edge-wound and/or may have a ribbon, rectangular, oblong, or other non-circular shaped cross-sectional shape.

Although the proximal coil 216 and distal coil 218 aid in filling some of the annular space, additional annular space remains, particularly when a somewhat larger tube 204 is utilized. The wire size of the proximal coil 216 and distal coil 218 could be increased to fill more space. However, increasing wire size too much may introduce excessive stiffness to the device. Preferably, the wire size of the proximal coil 216 and distal coil 218 is about 0.008 inches or less, or about 0.006 inches or less, or more preferably about 0.004 inches or less, such as about 0.002 inches or less.

To aid in filling the remainder of the annular space, the guidewire 200 may include a bushing coil 220. The bushing coil 220 may be disposed over the proximal coil 216 and the distal coil 218. The bushing coil 220 may extend over the entirety of both of the proximal coil 216 and the distal coil 218. As with the proximal coil 216 and the distal coil 218, the wire diameter of the bushing coil 220 is preferably limited. For example, the wire diameter of the bushing coil may be about 0.008 inches or less, or about 0.006 inches or less, or more preferably about 0.004 inches or less, such as about 0.002 inches or less. The bushing coil 220 may be formed of stainless steel and/or other suitable material, such as another metal or a polymer.

The use of a bushing coil 220 in addition to the proximal coil 216 and distal coil 218 aids in filling the annular space between the distal core 203 and the tube 204 without the use of over-sized coils. This aids in maintaining centering of the distal core 203 within the tube 204, which prevents the undesirable effects of misalignment that have been described above while also minimally impacting the bending flexibility of the device.

In some embodiments, the bushing coil 220 may be substantially coincident with the proximal coil 216 and the distal coil 218. Alternatively, as shown, the bushing coil 220 may extend farther proximally than the proximal coil 216. This allows the bushing coil 220 to fill in more of the annular space even at portions where the proximal coil 216 is not able. That is, because of the tapered profile of the distal core 203, certain more proximal portions of the annular space do not fit both the proximal coil 216 and the bushing coil 220, but may still be filled by the further extending proximal portion of the bushing coil 220. The bushing coil 220 preferably extends along a substantial portion of the length of the tube 204. For example, the bushing coil 220 may have a length of at least about 60% of the length of the tube 204, or at least about 75% of the length of the tube 204, or at least about 80% of the length of the tube 204, or at least about 85% of the length of the tube 204.

In preferred embodiments, the proximal coil 216 and the distal coil 218 are each wound in a first direction, while the bushing coil 220 is counter-wound in a second, opposite direction. This beneficially limits interlocking and binding of the bushing coil 220 to either of the proximal coil 216 or the distal coil 218. The bushing coil 220 may also have a pitch that is different (e.g., narrower) than that of the proximal coil 216 or the distal coil 218. For example, the proximal coil 216 and/or the distal coil 218 may have a pitch of about 0.002 inches to about 0.008 inches, or about 0.003 inches to about 0.007 inches, whereas the bushing coil 220 may have a pitch of about 0.001 inches to about 0.006 inches, or about 0.002 inches to about 0.005 inches.

The proximal coil 216, the distal coil 218, and the bushing coil 220 are preferably configured to fill a substantial portion of the volume of the annular space between the distal core 203 and the tube 204. For example, proximal coil 216, the distal coil 218, and the bushing coil 220 may be configured to fill approximately 20% or more, 35% or more, 50% or more, 60% or more, 70% or more, 80% or more, or even up to about 90% or more of the volume of the annular space. Of course, other conventional guidewires may include joints or bushings that fill up large portions of the annular space at the particular part of the guidewire they are located. However, when the entire length of the outer tube is considered, such joints and bushings fill relatively little of the volume of the overall annular space.

The centering mechanism principles described herein may be utilized with other structural configurations to provide beneficial centering effects. For example, while the above embodiments describe various centering mechanisms with a core as the "inner member" and a microfabricated tube as the "outer member," other structures may additionally or alternatively be utilized as the outer and/or inner members along with one or more of the described centering mechanisms.

For example, the inner member may be a wire (such as a ground core as described above), a tube (e.g., metal or polymer hypotube or metal or polymer microfabricated tube), a braid, or a coil. By way of further example, the outer member may be a tube (e.g., metal or polymer hypotube or metal or polymer microfabricated tube), a braid, a coil, or a polymer tube impregnated with a braid or coil. The centering mechanism may include a set of coils such as those described above, or may additionally or alternatively include other structures for providing centering of the inner member within the outer member. For example, one or more of the coils 216, 218, 220 may be replaced by one or more tubes (e.g., metal or polymer hypotube or metal or polymer microfabricated tube), braided sections, or sets of stacked rings.

Figure 4:
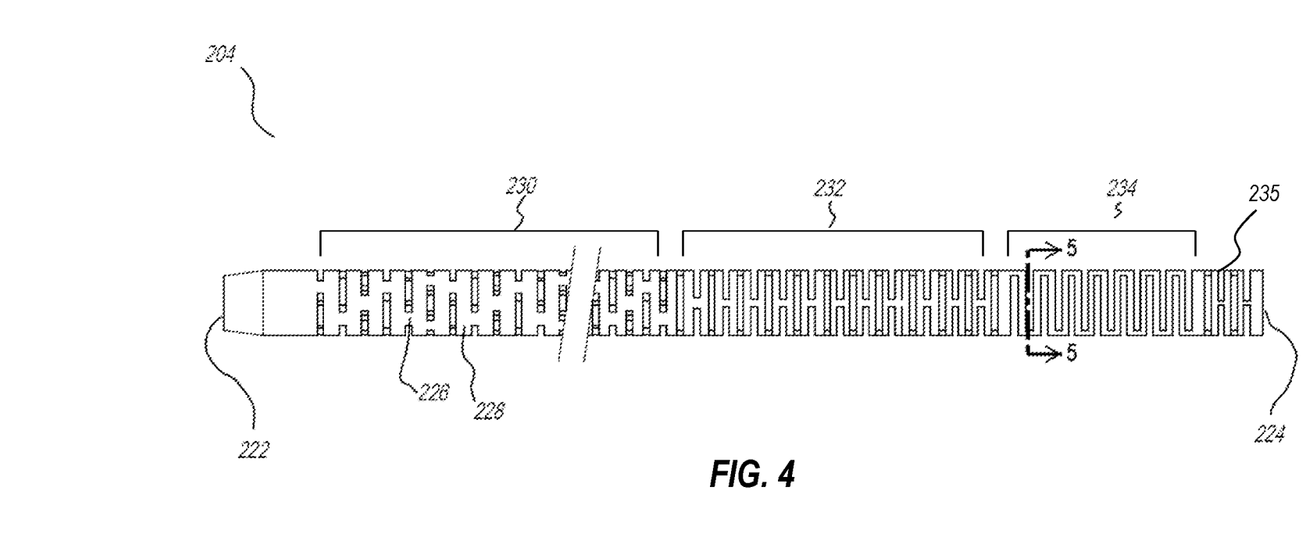
FIG. 4 is a detailed view of the tube of the guidewire of FIG. 2.

FIG. 4 illustrates the tube 204 separate from the core 202 and some of the other components of the device. The tube 204 extends between a proximal end 222 and a distal end 224. The fenestrations 206 formed within the tube 204 may be made according to a variety of cut patterns. Preferably, the overall effect of the fenestrations provides a flexibility gradient across the tube 204 where more flexibility increases closer to the distal end 224. Typically, greater flexibility can be provided by removing more of the stock material, such as by increasing the depth of the cut, decreasing the space between adjacent cuts, and/or reducing the number of axially extending beams 226 connecting each of the circumferentially extending rings 228.

The illustrated embodiment, for example, may include a three-beam section 230 (three beams connecting each adjacent pair of rings) that transitions to a two-beam section 232 (two beams connecting each adjacent pair of rings) that transitions to a one-beam section 234 (a single beam connecting each adjacent pair of rings). Within each of these sections, the cut depth and/or cut spacing may also be adjusted to provide a smooth intra-section and inter-section flexibility gradient. For example, the two-beam section 232 may have progressively less distance between cuts as it advances toward the distal end 224. It may then transition to the one-beam section 234, which itself then includes progressively less distance between cuts as it advances toward the distal end 224.

The one-beam section 234 may have a length of about 0.5 cm to about 3 cm, or about 0.75 cm to about 2 cm, for example. The two-beam section 232 may have a length of about 4 cm to about 16 cm, or about 6 cm to about 12 cm, for example. The three-beam section 230 may have a length of about 12 cm to about 36 cm, or about 18 cm to about 30 cm, for example. In other words, the three-beam section 230 may be about 2 to 5 times longer than the two-beam section 232, and the two-beam section 232 may be about 2 to 5 times longer than the one-beam section 234. Designing the tube 204 with these proportions of cut/beam sections has been found to provide effective balance of axial, lateral, and torsional stiffness for most applications.

The tube 204 may also include a distal-most section 235 that has a two-beam pattern. This section is preferably relatively short, such as about 0.5 cm or less, or about 0.25 cm or less, or about 0.15 cm or less. Providing a relatively short two-beam section at section 235 provides added surface area for an adhesive material applied at or near the distal end 224 of the tube 204 to bond, allowing a stronger coupling between the distal end 224 and any internal components bonded thereto.

Certain sections of the tube 204 may have cuts that are rotationally offset so as to avoid the formation of any preferred bending planes. For example, an angular offset may be applied after each cut or series of cuts such that the overall resulting pattern of beams 226 in the tube 204 do not align in a way that forms preferred bending planes.

Figure 5:
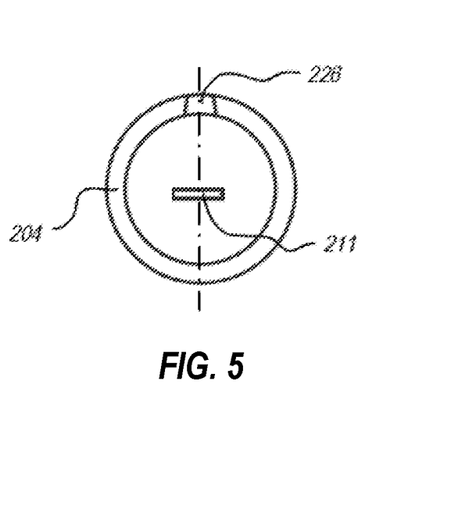
FIG. 5 is a cross-sectional view of a distal section of the guidewire of FIG. 2, showing alignment of the beams of a one-beam section of the tube with a flattened distal section of the core.

Other sections of the tube 204 may include a preferred bending plane. For example, the one-beam section 234 may be aligned as shown in FIG. 4, with each beam offset by about 180° from the previous beam. These beams may also be aligned with the bending plane of the flattened distal end section 211 of the core. FIG. 5 illustrates, in cross-section, how the beams 226 of the one-beam section 234 are preferably aligned in the same plane as the flattened, wider section of the distal end section 211 of the core.

CONCLUSION

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, or less than 1% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may include properties, features (e.g., ingredients, components, members, elements, parts, and/or portions) described in other embodiments described herein. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

The invention claimed is:

1. An intravascular device, comprising:
a core having a proximal section and a distal section;
an outer tube coupled to the core such that the distal section of the core passes into and is encompassed by the outer tube, the outer tube and the core defining an annular space between an inner surface of the outer tube and the distal section of the core disposed within the outer tube;
a distal coil encompassing part of the distal section of the core;
a proximal coil disposed proximal of the distal coil and encompassing part of the distal section of the core; and
a bushing coil disposed over at least a portion of the distal coil and over at least a portion of the proximal coil,
wherein the distal coil, proximal coil, and bushing coil fill at least a portion of the annular space,
wherein an outer diameter of the outer tube is greater than an outer diameter of the proximal section of the core, and
wherein the outer tube includes fenestrations that form a plurality of axially extending beams connecting circumferentially extending rings, wherein the fenestrations form a two-beam section proximal of a one-beam section proximal of a distal-most two-beam section.

2. The device of claim 1, wherein the distal coil is more radiopaque than stainless steel.

3. The device of claim 1, wherein the proximal coil is less radiopaque than the distal coil.

4. The device of claim 1, wherein a wire size of the distal coil, proximal coil, and/or bushing coil is about 0.006 inches or less.

5. The device of claim 1, wherein the bushing coil extends farther proximally than the proximal coil.

6. The device of claim 1, wherein the bushing coil has a length of at least about 60% of the length of the outer tube.

7. The device of claim 1, wherein at least one of the proximal coil, distal coil, and bushing coil is wound in a direction opposite the other coils.

8. The device of claim 7, wherein the proximal coil and the distal coil are each wound in a first direction, while the bushing coil is counter-wound in a second, opposite direction.

9. The device of claim 1, wherein the bushing coil has a pitch that is smaller than that of the proximal coil and/or distal coil.

10. The device of claim 1, wherein the proximal coil, distal coil, and bushing coil fill 50% or more of the volume of the annular space.

11. The device of claim 1, wherein the outer diameter of the outer tube is larger than the outer diameter of the proximal section of the core by 15% to 80%.

12. The device of claim 1, further comprising a bushing disposed at a proximal end of the outer tube to aid in coupling the outer tube to the core.

13. The device of claim 12, wherein the bushing comprises a chamfered or beveled proximal edge.

14. The device of claim 13, wherein the bushing also comprises a chamfered or beveled distal edge.

15. The device of claim 1, wherein the outer tube includes at least one of a three-beam section, a two-beam section, and a one-beam section.

16. The device of claim 1, wherein a flattened distal section of the core has a preferred bending plane and wherein the preferred bending plane of the flattened distal section is aligned with a preferred bending plane of a portion of the outer tube overlying the flattened distal section.

17. The device of claim 1, wherein the distal-most two-beam section is shorter than the one-beam section.

18. An intravascular device, comprising:
a core having a proximal section and a distal section;
an outer tube coupled to the core such that the distal section of the core passes into and is encompassed by the outer tube, the outer tube and the core defining an annular space between an inner surface of the outer tube and the distal section of the core disposed within the outer tube, wherein an outer diameter of the outer tube is greater than an outer diameter of the proximal section of the core;
a distal coil encompassing part of the distal section of the core;
a proximal coil disposed proximal of the distal coil and encompassing part of the distal section of the core;
a bushing coil disposed over the distal coil and the proximal coil; and
a bushing disposed at a proximal end of the outer tube to aid in coupling the outer tube to the core,
wherein the bushing comprises a chamfered or beveled proximal edge and a chamfered or beveled distal edge.

* * * * *